US009242246B2

(12) United States Patent
Simons et al.

(10) Patent No.: US 9,242,246 B2
(45) Date of Patent: Jan. 26, 2016

(54) SAMPLE RECEPTACLE

(75) Inventors: Daniel Simons, Aathal (CH); Dirk Leber, Schwaig (DE); Harald Quintel, Steckborn (CH); Sasa Lazevski, Solingen (DE); Bruno Walder, Riedikon (CH); Andreas Bretscher, Uster (CH); Thomas Voit, Hilden (DE)

(73) Assignee: QIAGEN GMBH, Hilden (DE)

(*) Notice: Subject to any disclaimer, the term of this patent is extended or adjusted under 35 U.S.C. 154(b) by 0 days.

(21) Appl. No.: 14/003,755

(22) PCT Filed: Mar. 9, 2012

(86) PCT No.: PCT/EP2012/054165

§ 371 (c)(1), (2), (4) Date: Nov. 7, 2013

(87) PCT Pub. No.: WO2012/123375

PCT Pub. Date: Sep. 20, 2012

(65) Prior Publication Data

US 2014/0056784 A1 Feb. 27, 2014

(30) Foreign Application Priority Data

Mar. 11, 2011 (EP) .................................... 11157906

(51) Int. Cl.

| | |
|---|---|
| ***G01N 15/06*** | (2006.01) |
| ***G01N 33/00*** | (2006.01) |
| ***G01N 33/48*** | (2006.01) |
| ***B01L 3/00*** | (2006.01) |
| ***B65D 39/06*** | (2006.01) |

(52) U.S. Cl.

CPC ............. *B01L 3/50825* (2013.01); *B65D 39/06* (2013.01); *B01L 2300/045* (2013.01)

(58) Field of Classification Search

CPC ........ G01N 15/06; G01N 33/00; G01N 33/48

USPC .......... 422/50, 68.1, 554, 547, 550, 561, 562, 422/549

See application file for complete search history.

(56) References Cited

U.S. PATENT DOCUMENTS

| | | | |
|---|---|---|---|
| 2,367,883 | A | 1/1945 | Miller |
| 8,312,781 | B2 | 11/2012 | Himmelsbach et al. |

FOREIGN PATENT DOCUMENTS

| | | |
|---|---|---|
| EP | 0 264 181 | 4/1988 |
| EP | 0 449 425 | 10/1991 |
| EP | 0 503 867 | 9/1992 |
| EP | 0 954 486 | 11/1999 |
| EP | 1 847 461 | 10/2007 |
| WO | 91/06483 | 5/1991 |
| WO | 97/10155 | 3/1997 |
| WO | 2009/047821 | 4/2009 |

OTHER PUBLICATIONS

International Search Report for PCT/EP2012/054165 Mail Jul. 12, 2012.

*Primary Examiner* — Brian J Sines

(74) *Attorney, Agent, or Firm* — Miles & Stockbridge PC

(57) ABSTRACT

The invention relates to a sample container, comprising a housing which forms a sample space for receiving a sample and has at least one circular opening which extends in a channel-shaped manner into the sample space, and further comprising a spherical closing element, wherein the diameter of the closing element only exceeds the diameter of the opening channel in at least one (closing) portion to such an extent that the closing element can be fixed in a force-locked manner by its largest circumference in the closing portion, wherein the spherical closing element is in contact with the housing, and the opening channel between the closing portion and the inner opening forms a protrusion which reduces the opening cross section of the opening channel with respect to the opening cross section in the closing portion.

13 Claims, 19 Drawing Sheets

SAMPLE RECEPTACLE

CROSS REFERENCE TO RELATED APPLICATIONS

This application is a §371 National Stage Application of PCT/EP2012/054165, filed Mar. 9, 2012, which claims priority to European Application No. 11157906.6, filed Mar. 11, 2011.

BACKGROUND OF THE INVENTION

1. Field of the Invention

The invention relates to a sample container, comprising a housing which forms a sample space for receiving a sample and has at least one circular opening, and also comprising a spherical closing element.

2. Description of Related Art

Sample containers of this type are used in particular within the scope of biotechnological methods in order to process a biological sample or a biological material, such as a sample containing nucleic acids. These sample containers are used for example to duplicate nucleic acids in vitro within the scope of amplification reactions, such as a polymerase chain reaction (PCR). Here, the sample containers are used to receive the sample comprising the nucleic acid.

A large number of different sample containers that are routinely used as disposable products within the scope of appropriate biotechnological methods, such as PCR, are known from the prior art. Here, the sample containers are firstly filled with the sample, then closed in an airtight manner, and lastly supplied to the PCR process. Here, high demands are placed on the closure of the sample containers. On the one hand, the sample containers have to be reliably tightly sealed so as not to compromise the result of the PCR process by the undesired entry or exit of sample material. On the other hand, a large number of sample containers are routinely used within the scope of a PCR process and have to be filled and closed for this purpose. This should therefore be performed in an automated manner where possible. Furthermore, it must be possible to produce the sample containers cost-effectively, in particular because they are required in high number and are used as disposable products.

A generic sample container is known from EP 0 449 425 A2, wherein one end of a cylindrical housing, which forms a sample space, is provided with a circular opening that extends in a channel-shaped manner into the sample space. The opening channel tapers shortly before the transition into the sample space and thus forms a seal seat for a spherical closing element. Once the closing element has been fitted onto the seal seat, it is fixed by means of a closing plug.

As a three-part system, the sample container known from EP 0 449 425 A2 is not only relatively complex and therefore expensive, but can also only be closed in an automated manner with relatively high effort.

SUMMARY

Proceeding from this prior art, the object of the invention was to specify an improved sample container. In particular, the sample container according to the invention should be producible cost-effectively and closable in an automated manner with relatively little effort. At the same time, the sample container according to the invention should have a reliable sealing effect.

This object is achieved by a sample container according to independent claim 1. Advantageous developments are disclosed in the dependent claims and will emerge from the following description of the invention.

The core of the invention lies in implementing the functions, implemented by two different functional elements in the case of the sample container according to EP 0 449 425 A2, of sealing and also fixing the closing element by just one functional element, specifically the closing element itself. This is achieved by wedging a spherical closing element in an opening channel of a housing of the sample container according to the invention such that not only can a good sealing effect be achieved, but also reliable fixing. In contrast to the sample container known from EP 0 449 425 A2, it is thus possible to dispense with an additional closing plug in order to fix the closing body.

A sample container according to the invention therefore comprises a housing which forms a sample space for receiving a sample and also a spherical opening, which extends in a channel-shaped manner into the sample space. Furthermore, the sample container according to the invention comprises a spherical closing element. The (largest) diameter of the closing element is selected such that it exceeds the diameter of the opening channel in at least one (closing) portion of the opening channel, but only to an extent that allows the closing element to be introduced so far into the closing portion of the opening channel that the force-locked fixing is achieved by contact between a region comprising the largest circumference of the closing element and the closing portion. The spherical closing element is in contact with the housing. Further, the opening channel between the closing portion and the inner opening forms a (first) protrusion, which reduces the opening cross section of the opening channel with respect to the opening cross section in the closing portion. A one-piece closure can be formed by the direct contact between the closing element and the housing. Due to the formation of a one-piece closing element and the embodiment of the opening channel with the (first) protrusion, a cost-effective production of the sample container with closing element can be achieved, said sample container being closable in an automated manner with relatively little effort, wherein a reliable sealing effect is present. The (first) protrusion can be used as an end stop which prevents the closing element from being pressed beyond the closing portion into the sample space during the introduction process.

The force-locked fixing of the closing element by contact between a region comprising the largest circumference of the spherical closing element and the wall of the opening channel is important in order to achieve a secure fixing. The resultant forces with this type of force-locked fixing specifically comprise no, or only a relatively small (and therefore negligible), force components in the longitudinal axial direction of the opening channel; rather, these are directed (largely) radially in the direction of the centre of the spherical closing element. Sufficient fixing and, at the same time, a good sealing effect can thus be produced with only a relatively small (preferably elastic) deformation of the closing element and of the wall of the opening channel. A small deformation then also requires only relatively small forces in order to introduce the closing element into the opening channel. This can simplify the automation of the closing of the sample container and can also enable manual closing of the sample container. In addition, the requirements of the materials used for the closing element and the housing are reduced, whereby the production costs for the sample container can be kept low.

In the case of the sample container in EP 0 449 425 A2, the diameter of the closing element indeed also exceeds the smallest diameter of the opening channel, but deliberately to such an extent that a seal seat is formed, on which the closing element sits. The good sealing effect of such a seal seat has indeed long been known, but requires an additional closing element which generates sufficiently high forces in the longitudinal axial direction of the opening channel in order to press the spherical closing element into the seal seat and therefore achieve the desired sealing effect. If these forces are so high that they result in a technically relevant elastic deformation of the closing element or of the wall of the opening channel, a force-locked fixing can also be achieved in the case of the sample container according to EP 0 449 425 A2 (if only to a small extent), but, since it does not act on the largest circumference of the spherical closing element, it always has a component in the longitudinal axial direction of the opening channel. This longitudinal axial force component is additionally directed such that, provided it exceeds the frictional forces of the closing element with the opening channel in the region of the ball seat, for example by means of an additional action of an overpressure prevailing inside the sample space, it lifts the closing element from the seal seat and the sample container therefore opens undesirably. An increase of the frictional forces without a simultaneous increase of the longitudinal axial force component is not possible, and therefore the sample container known from EP 0 449 425 A2 cannot be reliably closed without the additional closing plug.

The materials and also the dimensions of the closing element and of the housing in the region of the closing portion can be selected purposefully with regard to the desired deformation behavior. A ball that is soft compared to the housing (and therefore deforms to a considerably greater extent compared to the housing) may have advantages when it comes to the sealing effect. This advantage may also be contrasted however by disadvantages with regard to the positioning (checking) and the material selection. By contrast, a ball that is hard compared to the housing can be well handled during the introduction process and enables easier positioning and position checking, but may entail the risk of an overstretching of the housing (into the plastic range).

DETAILED DESCRIPTION OF A PREFERRED EMBODIMENT

Figure 1:
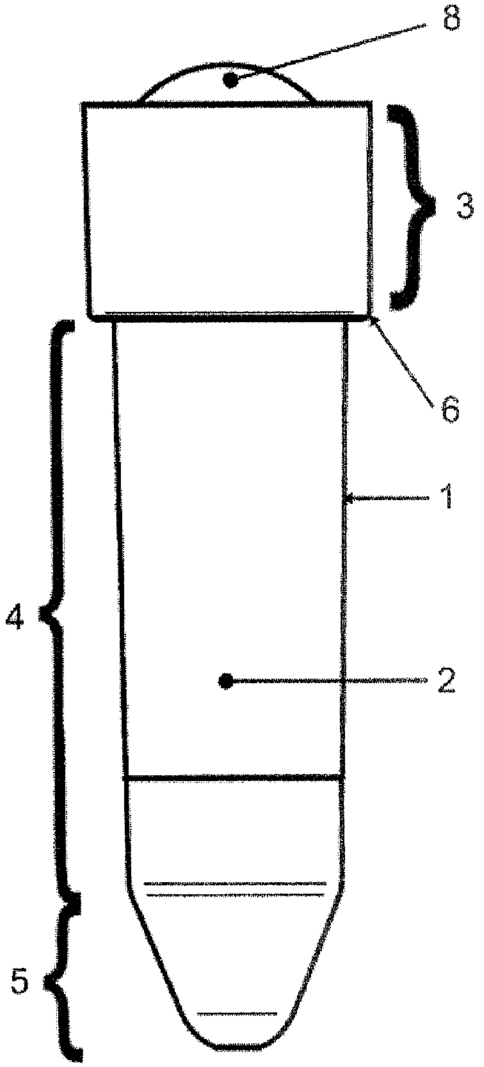
FIGS. 1-20*f* represent embodiments as described herein.

In accordance with a preferred embodiment of the sample container according to the invention, the opening channel between the closing portion and the outer opening may form a (second or further) protrusion, which reduces the opening cross section of the opening channel with respect to the opening cross section in the closing portion. Such a protrusion, which for example can be formed in a (closed) annular manner or also by one or more individual protrusions, preferably arranged side by side annularly, can be used in particular as a securing stop in order to prevent an undesirable release of the closing element from the closing portion of the opening channel, for example as a result of an unexpectedly high pressure increase in the sample space, which for example may be caused by heating within the scope of the PCR process. Should the pressure increase within the sample space be so high that the force-locked connection of the closing element held in the closing portion is overcome, the closing element, possibly after a slight shift within the closing portion of the opening channel, can thus be supported against the protrusion, whereby a reliable and in particular tight closure of the sample container can also be achieved.

Since the (second or further) protrusion has to be passed by the closing element when closing the sample container, it may be dimensioned such that the closing element is introduced into the closing portion with exertion of a defined press-in force, which should not be so great that it damages the closing element or the housing of the sample container as a result of an excessively high deformation, but is greater than the maximum anticipated force caused by a pressure increase in the sample space.

The opening cross section of the opening channel in the region of the (second) protrusion is preferably also larger than in the region of the first protrusion. As a result, the force that is applied in order to press the closing element into the opening channel can be sufficiently high for the closing element to pass the second protrusion, but not so high that it can also pass the first protrusion.

In a further preferred embodiment of the sample container according to the invention, the distance between the first and the second closing element can also be dimensioned in accordance with the dimensions of the closing element such that a positioning tolerance of the closing element within the closing portion of at most 5 mm and in particular of at most 0.7 mm is provided. This means that the closing element is displaceable merely over this distance between the two protrusions. A displacement of the closing element beyond this maximum distance, in particular due to a pressure increase within the sample space, generally leads to a tolerable modification of the process conditions, for example of a PCR process. At the same time, it is possible to avoid the fact that a higher tolerance for manufacturing the sample container has to be observed, which could increase the cost of the sample container.

The opening channel is preferably cylindrical in the region of the closing portion. Irrespective of the actual position of the closing element in the closing portion, a force-locked fixing and sealing effect of substantially identical magnitude is thus always achieved. Where appropriate, the opening channel may be formed slightly conically (for example with an angle of slope from 0.1 to 0.5°) (also) in the closing portion, which can facilitate demolding when producing the housing by means of casting and in particular injection molding. The angle of slope can be selected to be so small that it has no significant (negative) influence on the fixing and sealing effect of the wedged closing element.

The housing of the sample container according to the invention may preferably be tubular (also in a stepped manner), wherein the opening is arranged at a (longitudinal axial) end of the housing. Furthermore, the housing can preferably be formed in a tapering manner at the second end, whereby even very small sample quantities can be effectively concentrated in the sample space, which can facilitate the execution of the biotechnological method, for example a PCR process.

In order to enable an examination of the sample by means of optical methods (including a purely visual inspection), the housing of the sample container may also be formed at least in part of an optically transparent material. In particular, the tapering end can be optically transparent, since this end is preferably used to receive the sample.

Furthermore, the housing may preferably be formed, in the region that is used to receive the sample, with a thinner wall thickness compared to a (or at least one) second region of the housing forming the sample space. A wall thickness that is as thin as possible can simplify the examination of the sample by means of optical methods, whereas a thicker wall thickness, in particular in a dead space of the sample space, which is not filled with the sample, can avoid or reduce an evaporation through the housing, which is preferably fabricated from plastic.

Furthermore, the housing, in the closing portion of the opening channel, may also be formed from an (optically) transparent material. This makes it possible to check the position of the closing element in the closing portion and additionally the sealing effect by means of optical means (including a purely visual inspection). For checking by machine, a change to the refractive index for example can be used, this change being caused by the fact that, during the transition from a first solid (wall of the opening channel) to a second solid (closing element), there is no total reflection of the light at the inner wall, and, in the event of transition from a solid (wall of the opening channel) to air, the inner face of the opening channel reflects in part, by contrast.

The housing may further preferably form a shoulder for forming a bearing surface. The forces that are to be applied to press in the closing element (typically up to 60 N to 130 N and at most 250 N) can be supported at a holder supporting the sample container via said bearing surface. In particular, the bearing surface can be formed at a point of the housing that is located in the vicinity of the closing portion of the opening channel. It is thus possible to prevent the forces from being transmitted via other portions of the housing, which may be formed with thinner wall thicknesses and may therefore be more sensitive (in particular the wall of the housing surrounding the sample space).

Furthermore, the housing of the sample container, at least in the closing portion of the opening channel, and/or the closing element itself may be formed from a material having minimal coefficients of thermal expansion and particularly preferably having identical coefficients of expansion where possible. It is thus possible to prevent the pressing in the contact area between the closing element and the wall of the opening channel from being changed as a result of heating, for example caused during a PCR process, whereby not only the fixing of the closing element, but also the sealing effect thereof, could be changed in equal measure.

In a preferred embodiment of the sample container according to the invention, the closing element can be formed from an electrically conductive material. Not only can an electrostatic charging of the ball thus be avoided, which could impair the handling of the sample container, but the conductivity may also make it possible to detect the position of the closing element within the opening channel and/or the sealing effects in a contact-based manner or also contactlessly, for example capacitively or inductively.

The closing element of the sample container according to the invention is preferably formed from a material that has no or only low (in particular technically irrelevant) inherent fluorescence. As a result, a monitoring of the biotechnological method, such as of the PCR process, based on the measurement of the fluorescence of the sample cannot be negatively impaired.

In order to enable easy opening of the sample container after use, said sample container can be provided with a predetermined breaking point, at which the housing is separated by a defined application of force. This type of opening is suitable in particular for sample containers that are to be used just once (disposable sample container). An advantage of this embodiment of the sample container according to the invention may lie in particular in the fact that the process of opening can be less complex than a removal of the closing element fixed in the closing portion of the opening channel, which is likewise possible however. Instead of a predetermined breaking point, it is also possible to form the housing in two parts, wherein the two parts can be interconnected for example via a plug or detent connection. To open the closed sample container, the housing can then be opened again at this connection point.

The sample container can also be opened by pushing the closing element into the sample space. For this purpose, the sample space should, at least in one portion, have a larger cross-sectional area than the closing element in order to be able to empty the sample space.

In some applications, sample containers that are used within the scope of the respective biotechnological method (such as a PCR process) are not to be opened again. In order to ensure a permanent closure of the sample container according to the invention, the closing element, in accordance with the invention, may additionally be secured in the closing portion, for example, with suitable material selection, by being welded to the wall of the housing (for example by means of ultrasonic welding or thermal welding) or by being fixed in a form-fitting manner by means of the flanging of an upper edge of the housing. Of course, any other types of additional form-fit, force-locked or integrally bonded fixing are possible.

In a preferred embodiment of the sample container according to the invention, a second closing portion for a second closing element may also be provided, wherein a second sample space is formed between the two closing elements. All developments previously presented with regard to the first closing portion and/or the first closing element can also be provided here for the second closing portion and/or the second closing element.

Preferably, a (or at least one) bypass channel can be provided in the wall of the housing between the two closing portions of the sample container. This bypass channel can be used to avoid an overpressure otherwise created in the lower sample space as a result of the introduction of one closing element as far as the lower closing portion and to transfer the upper sample material into the lower sample space by pressing down the upper closing element.

The present invention further relates to a method for preparing or processing a biological sample or a biological material, in particular a sample containing nucleic acids, wherein the sample container according to the invention is used. The sample container according to the invention is described in detail in the description and the claims. Reference is made to the corresponding disclosure. The method may in particular be a biotechnological method, such as an amplification method, in particular a PCR method.

The invention will be explained in greater detail hereinafter on the basis of exemplary embodiments illustrated in the drawings.

Figure 2:
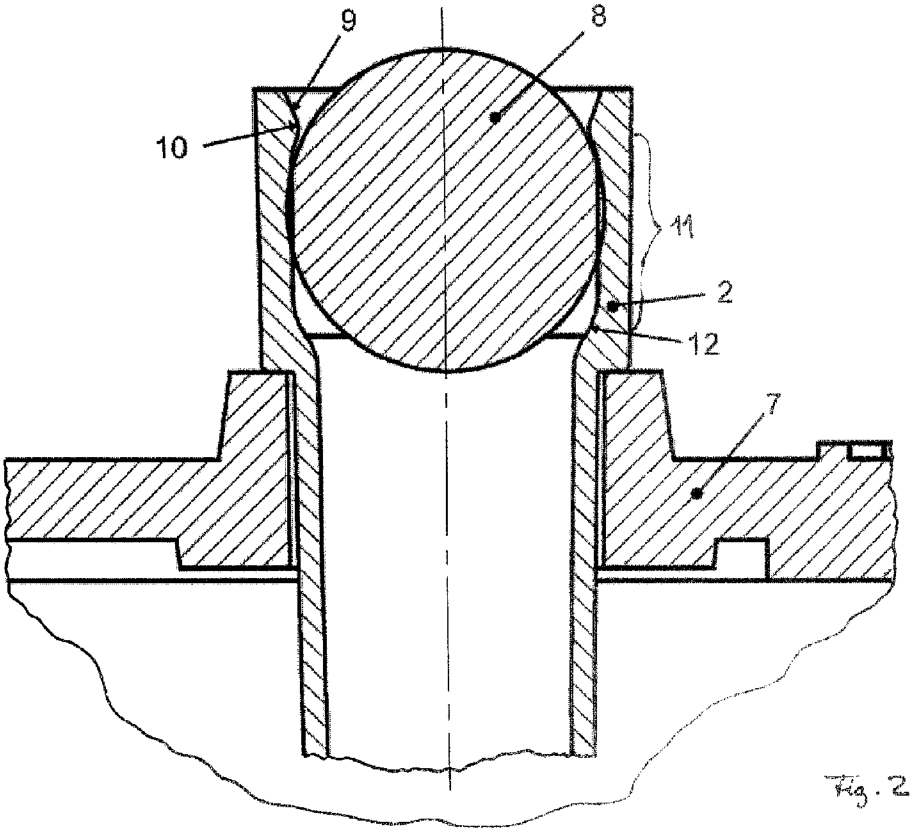
Figure 3:
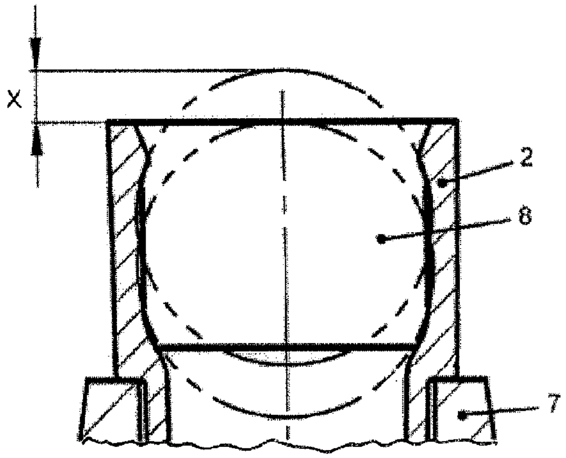
Figure 4:
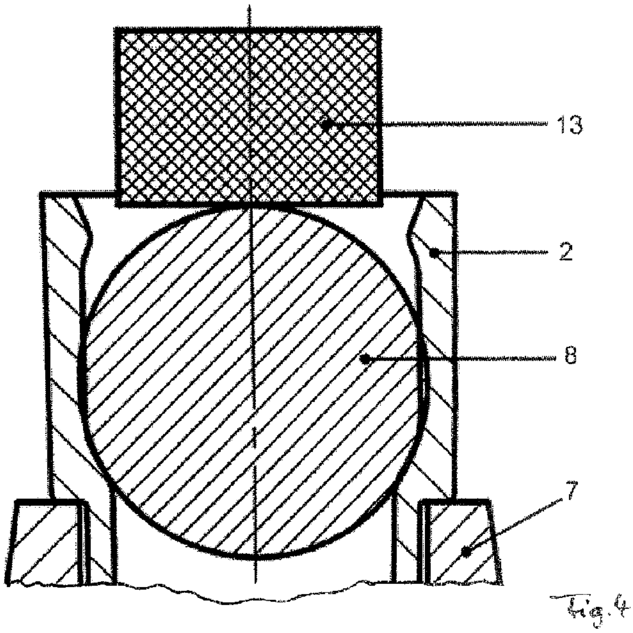
Figure 5:
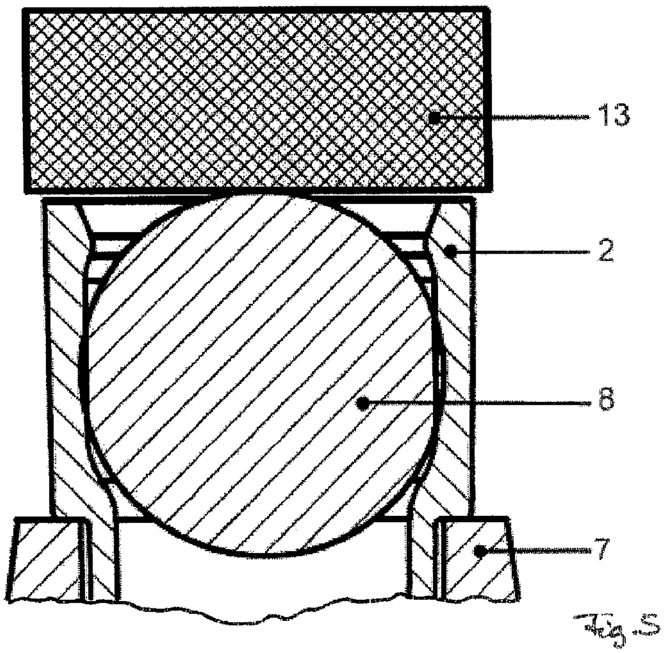
Figure 6:
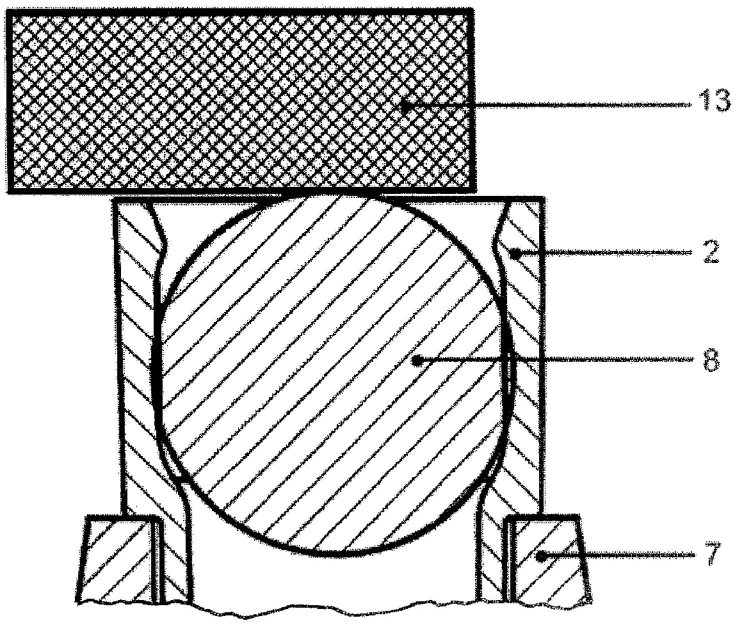
Figure 7A:
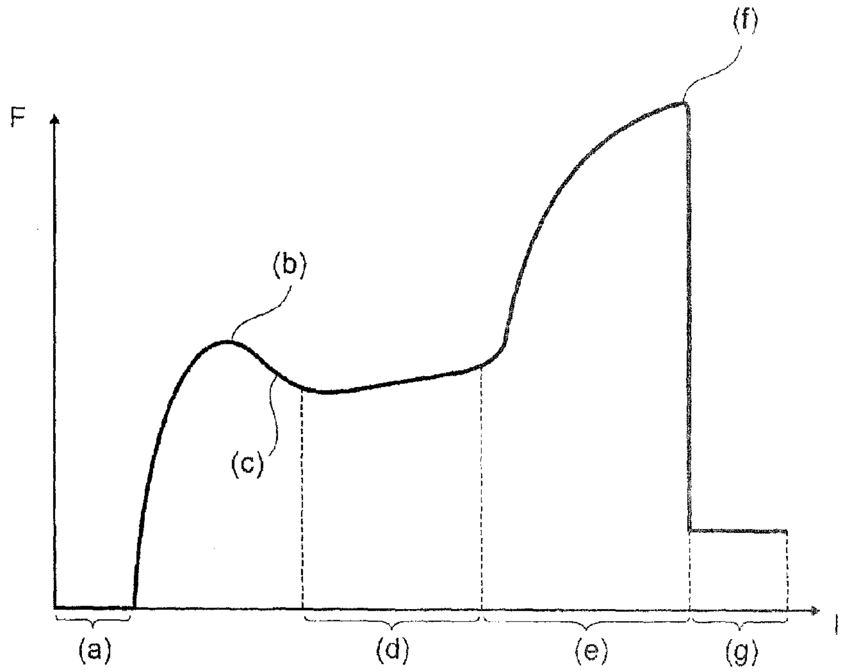
Figure 7B:
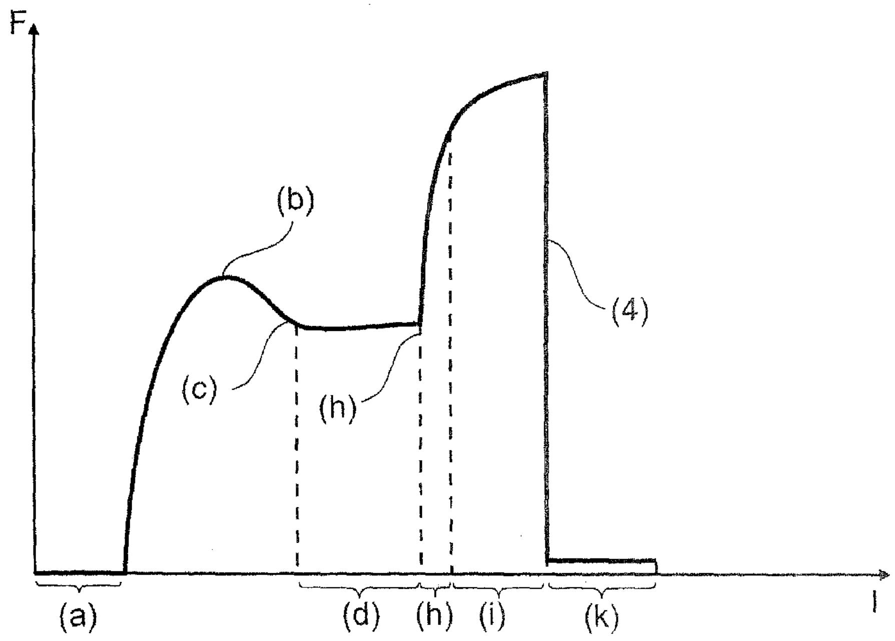
Figure 8A:
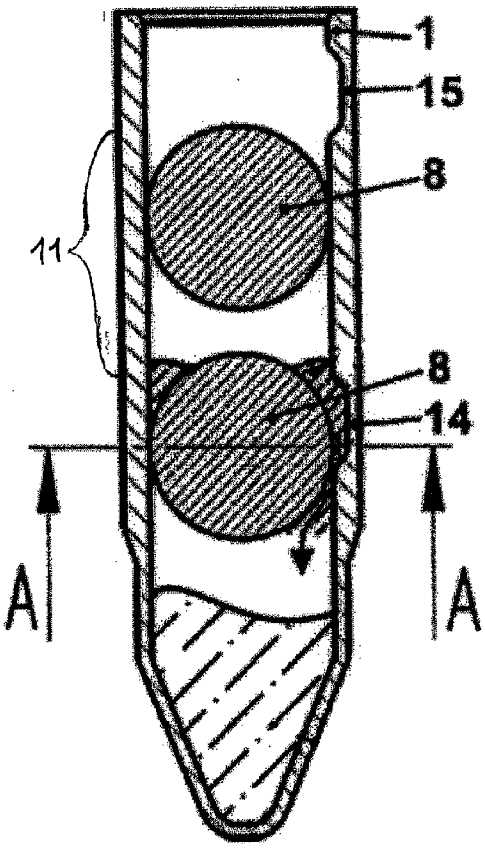
Figure 8B:
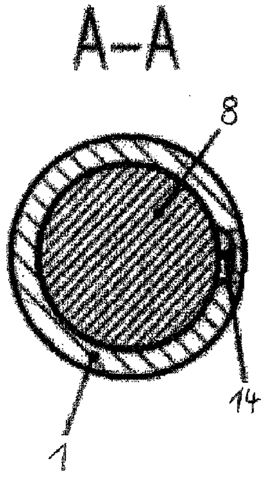
Figure 9A:
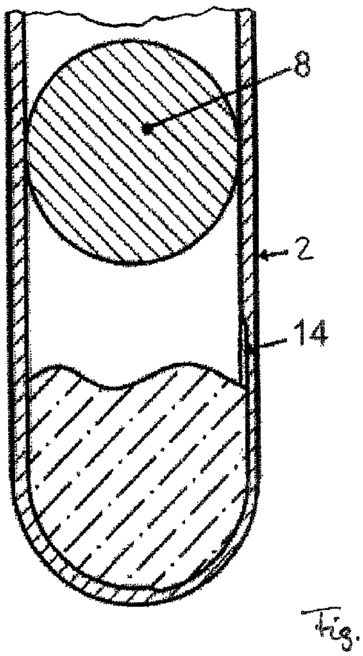
Figure 9B:
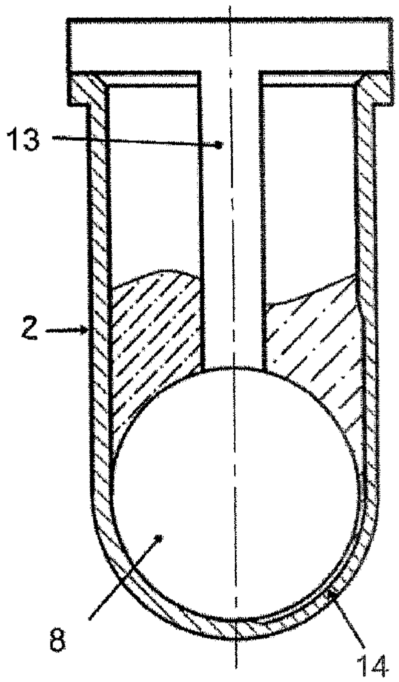
Figure 10:
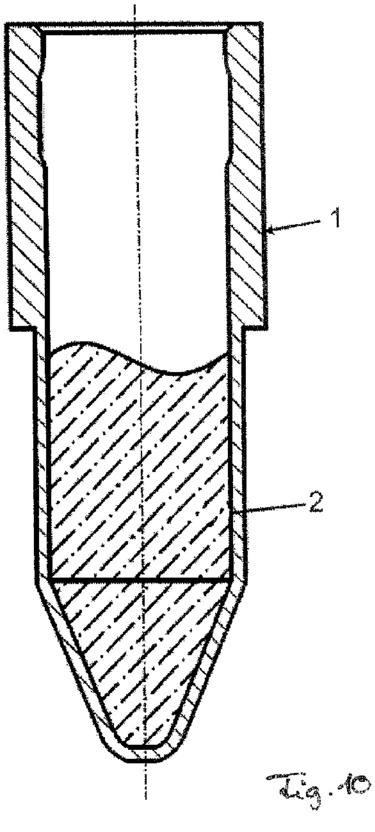
Figure 11:
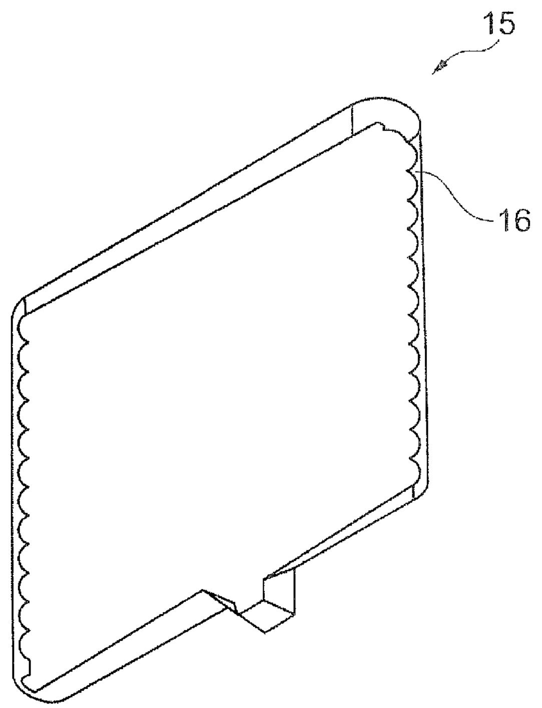
Figure 12:
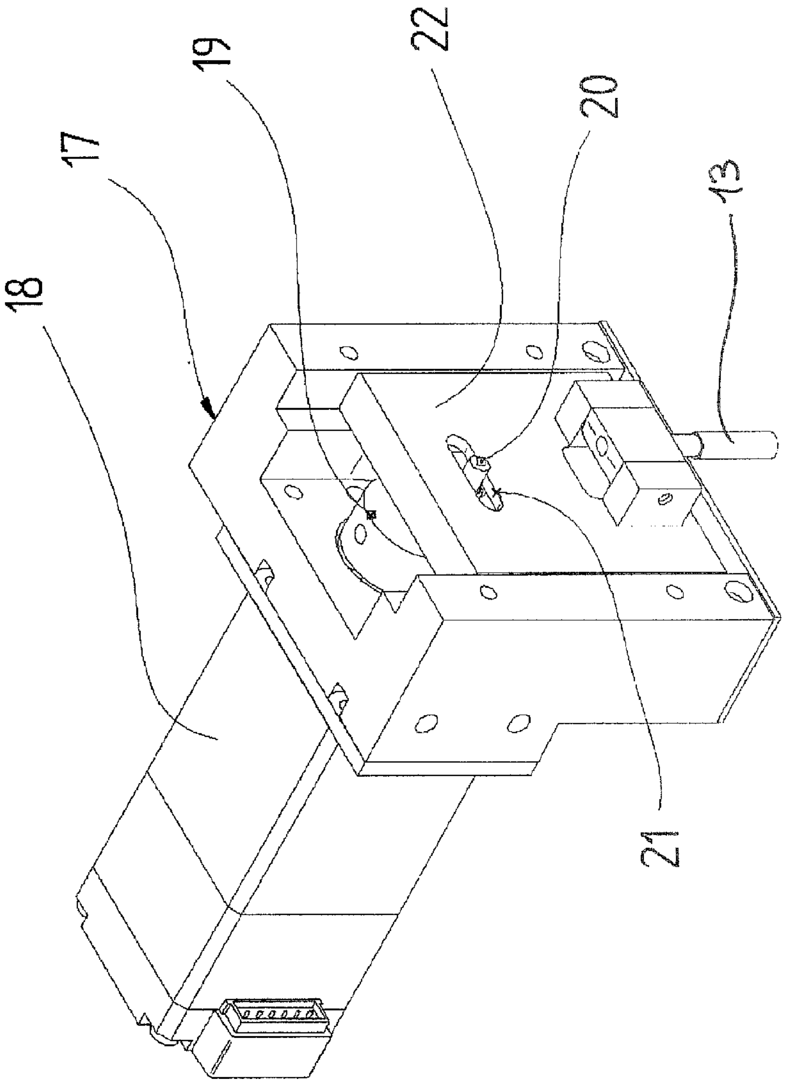
Figure 13:
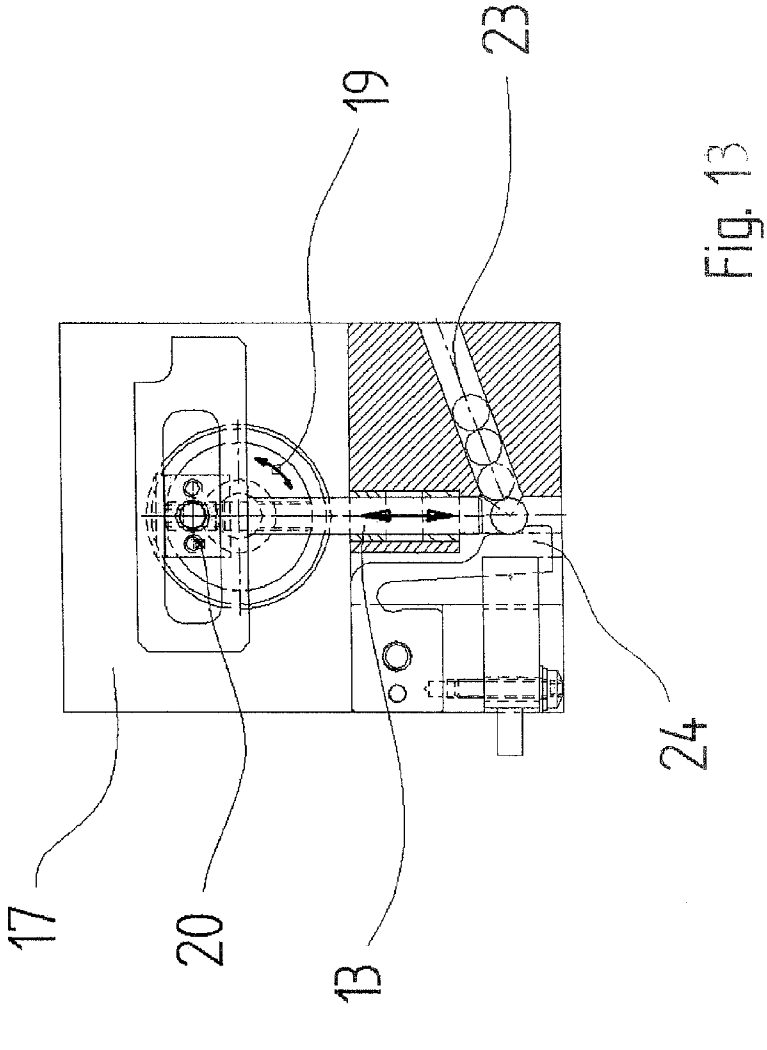
Figure 14:
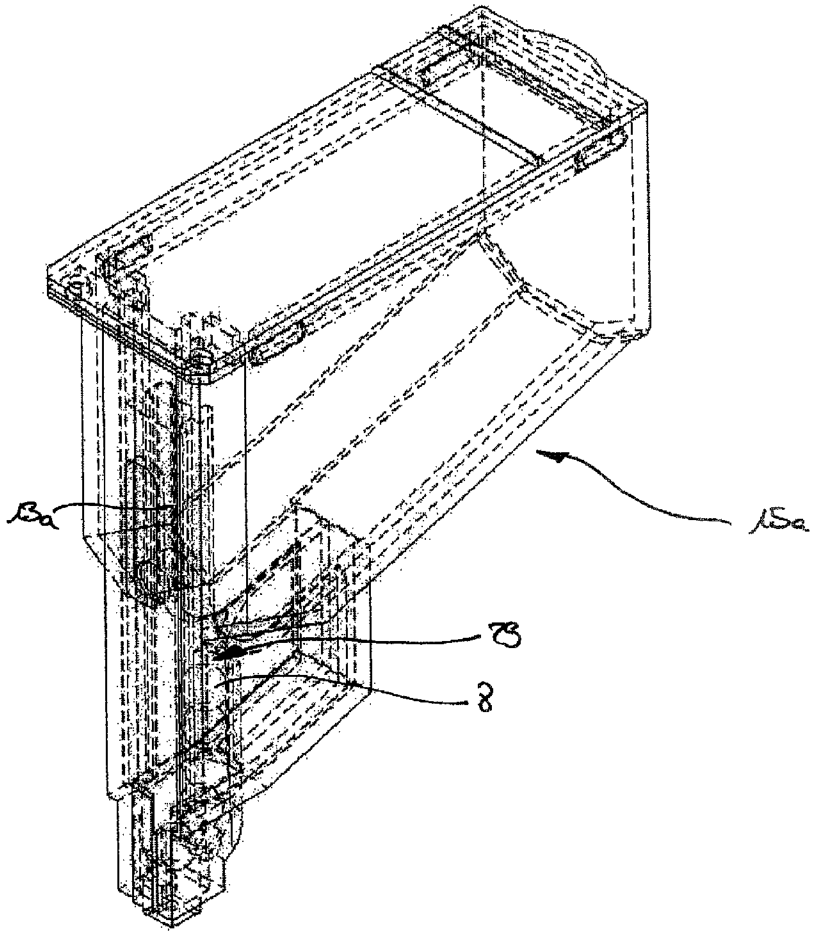
Figure 15:
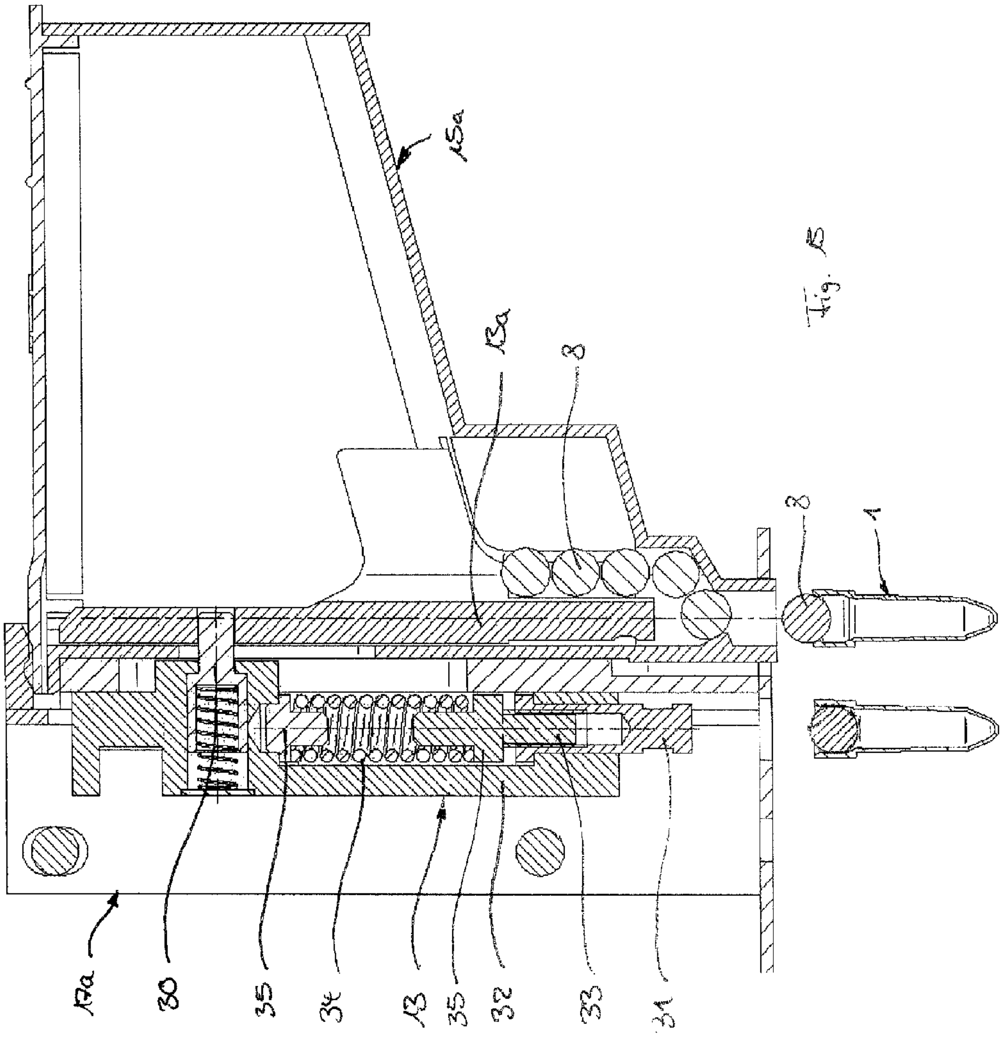
Figure 16:
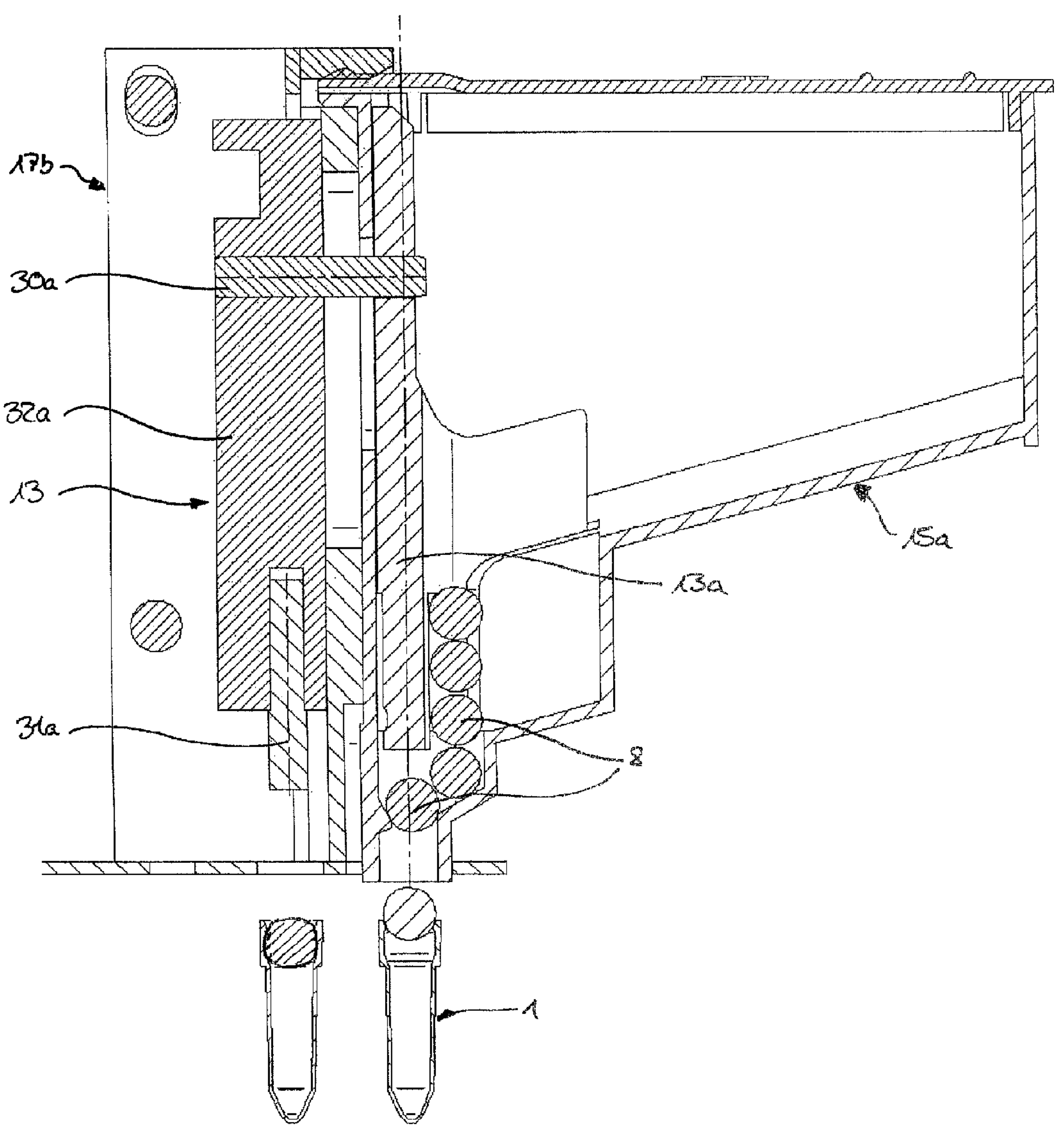
Figure 17:
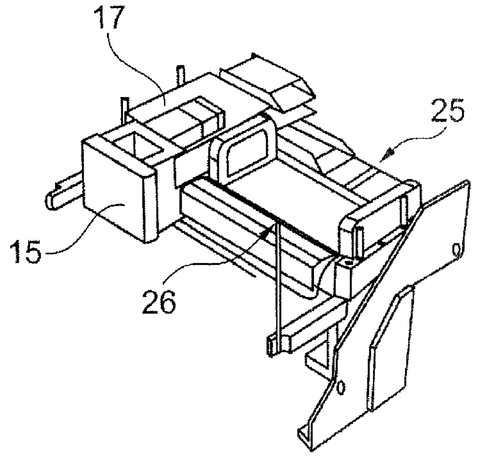
Figure 18:
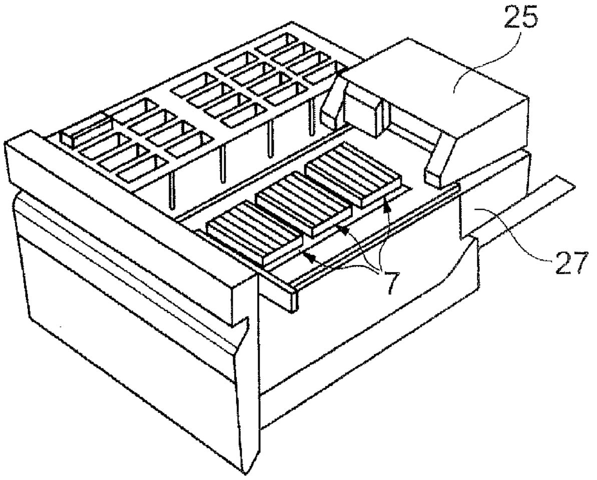

In the drawings:

FIG. 1: shows a sample container of a system according to the invention;

FIG. 2: shows a detail of the sample container of FIG. 1 in a sectional side view;

FIG. 3: shows a further detail of the sample container of FIG. 1 in a sectional side view;

FIG. 4: shows the introduction of the closing element into the sample container according to FIGS. 1 to 3 by means of a ram in a first embodiment;

FIGS. 5 and 6: show the introduction of a closing element into a sample container according to FIG. 1 by means of a ram in a second embodiment;

FIG. 7*a*: shows the force curve when introducing closing elements into sample containers according to FIGS. 1 to 3 with use of a ram according to FIG. 4;

FIG. 7*b*: shows the force curve when introducing closing elements into sample containers according to FIGS. 1 to 3 with use of a ram according to FIGS. 5 and 6;

FIGS. 8*a* and 8*b*: show a sample container of a system according to the invention in a second embodiment in two different sectional illustrations;

FIGS. 9*a* and 9*b*: show a sample container of a system according to the invention in a third embodiment;

FIG. 10: shows a sample container of a system according to the invention in a fourth embodiment;

FIG. 11: shows a storage container of a device according to the invention for automatically closing sample containers in a first embodiment;

FIG. 12: shows a closing unit of a device for the automated closing of sample containers according to the invention;

FIG. 13: shows a basic illustration of the operating principle of the closing unit according to FIG. 12;

FIG. 14: shows an isometric view of a storage container of a device according to the invention for automatically closing sample containers in a second embodiment;

FIG. 15: shows the storage container according to FIG. 14 in combination with a closing unit in a longitudinal section;

FIG. 16: shows the storage container according to FIG. 14 in combination with an alternative closing unit in a longitudinal section;

FIG. 17: shows the integration of the components according to FIGS. 11 and 12 in an automated closing device;

FIG. 18: shows the integration of the automated closing device according to FIG. 17 in a device for carrying out a PCR;

FIG. 18: shows a schematic illustration of an alternative supply of closing elements to a device for the automated closing of sample containers according to the invention; and FIGS. 20*a* to 20*f*: show comparisons of a "normal" force curve to deviating force curves, produced by various causes.

FIG. 1 shows a sample container 1 according to the invention in a first embodiment. The sample container 1 comprises a housing 2, which is formed in a first portion (head portion 3) and a second portion (middle portion 4) with a largely cylindrical lateral surface. The lateral surface has just a small conical tapering, which is used in order to more easily demold the housing 2 consisting of plastic after injection molding. The end of the middle portion 4 opposite the head portion 3 is adjoined by an end portion 5, in which the housing 2 tapers and is therefore formed in a tapering manner in the broader sense. In the end portion 5, the housing 2 is formed from an (optically) transparent material, which enables the use of optical measuring elements within the scope of a biotechnological method, such as a PCR process, in which the sample container 1 is to be used.

On the outer face between the head portion 3 and the middle portion 4, the housing 2 forms a shoulder 6, which is used as a bearing surface, via which the housing 2 is supported on a sample container support 7 (see FIG. 2).

Within the middle portion 4 and the end portion 5 of the housing 2, a sample space is formed, wherein the wall thickness of the housing 2 in these two portions is largely constant, such that a sample space portion which is again largely cylindrical is formed within the middle portion 4, and a conically tapering sample space portion formed with a rounded tip is formed in the end portion 5 of the housing 2.

In the head portion 3 of the housing 2, an opening channel is formed, which makes it possible to fill the sample container 1 with the sample to be examined. After filling, the sample space is closed by the introduction of a spherical closing element 8 in the manner according to the invention. The closing effect, that is to say both the sealing and the fixing of the closing element 8 in the opening channel, is achieved in that the largest outer diameter of the closing element 8 is slightly larger than the opening channel in a defined portion (closing portion 11) (see FIG. 2) and the closing element 8 is therefore fixed in a wedged manner in the opening channel.

Starting from the upper (free) end of the head portion 3, the opening channel is first provided with an entry chamfer 9, which defines a relatively (based on the outer diameter of the closing element 8) large opening cross section (largest diameter: 4.5 mm). The entry chamfer 9 facilitates the central positioning of the closing element 8 (largest diameter 4.1 mm to 4.2 mm). The entry chamfer 9 transitions into a first annular protrusion 10, which reduces the opening cross section (diameter: 3.7 mm) of the opening channel compared to the opening cross section in the closing portion of the opening channel (diameter: approximately 4.0 mm). In order to introduce the closing element 8 into the opening channel, it is loaded by a force (component) which is directed coaxially with or parallel to the longitudinal axis of the housing 2, specifically in the direction of the end portion of the housing 2.

The force is so great that it leads to a deformation both of the housing 2 in the region of the head portion 3 and of the closing element 8 itself, which makes it possible for the closing element 8 to pass the first protrusion 10 and to be inserted as far as the closing portion 11 of the opening channel. There, the closing element 8 is fixed in a force-locked manner, that is to say wedged, by means of its larger (maximum) diameter compared to the diameter of the opening channel in the closing portion 11. Here, the forces are achieved by a (largely elastic) deformation of the housing 2 in the region of the closing portion 11 and also of the closing element 8. Due to the symmetrical force-locked fixing of the spherical closing element 8 in the region of its largest cross section, the reaction forces that act from the wall of the opening channel onto the ball (and vice versa) do not have any component in the longitudinal axial direction of the housing. Once introduced into the closing portion 11, the closing element 8 is thus securely held, provided no significant external forces act thereon in the longitudinal direction of the housing 2.

The first protrusion 10, which has to be passed by the closing element 8 when introduced into the closing portion 11, is used on the one hand as an end stop that prevents the closing element 8 from being slid out from the opening channel in the event of the creation of an overpressure within the closed sample space, for example caused by heating within the scope of a biotechnological method, such as a PCR process, and thus prevents the sample container 1 from being opened undesirably.

Furthermore, this protrusion 10 is used to produce a force curve which is characteristic as the closing element 8 is introduced and on the basis of which an actual introduction of the closing element 8 as far as the closing portion 11 can be detected (in the manner of a locking into place).

The transition of the opening channel into the sample space of the housing 2 is formed as an annular shoulder. This shoulder constitutes a second protrusion 12, which is used as an end stop for the closing element 8 and therefore delimits the closing portion 11 of the opening channel on the side of the sample space.

The length of the closing portion 11 of the opening channel is dimensioned such that the closing element 8 can be displaced therein over a specific distance x before it contacts one of the two protrusions 11, 12 (see FIG. 3). This distance is limited in the present case to 0.7 mm at most, since experience has demonstrated that, with a displacement of this type of the closing element 8, the process parameters (in particular pressure, temperature) within the sample space only change to such a small extent that no significant (negative) effects on the biotechnological method, such as the PCR process, are to be feared. This positional tolerance of the closing element 8 within the closing portion 11 also has the advantage that relatively large tolerances in the production of the housing 2 and of the closing element 8 can be specified, whereby the corresponding tools can be subject to less stringent requirements.

FIGS. 4 to 6 show the use of a ram 13 (in two embodiments) in order to slide the closing element 8 into the opening channel. In the embodiment according to FIG. 4, the ram 13 has an outer diameter of 3.6 mm (or smaller), which is therefore smaller than the inner diameter of the opening channel in the region of the first protrusion 11. The ram 13 can therefore dip into the opening channel. To this end, the movement of the ram should be controllable in a precise manner in order to prevent said ram from pressing the closing element 8 with force against the second protrusion serving as an end stop, which could lead to damage of the housing 2 or of the closing element 8. In the embodiment of a ram 13 according to FIGS. 5 and 6, the outer diameter of the ram 3 is therefore considerably larger than the inner diameter of the opening channel in the region of the entry chamfer 9. The movement of the ram 13 is therefore delimited at the latest by the fact that it contacts the free end of the housing 2. A pressing of the closing element 8 by means of the ram against the second protrusion 12 serving as an end stop can therefore be easily avoided. A further advantage of the large contact area of the ram 13 is that the closing element 8 can be pressed in steadily without difficulty, even if the ram 13 is not arranged exactly centrally above the closing element 8 (see FIG. 6).

FIG. 7*a* shows an exemplary force curve (force F over the ram path I) for a closing process with use of a ram according to FIG. 4. In a first portion (a) of the force curve, the force is practically zero; this portion defines the displacement of the ram 13 until it contacts the closing element 8. This is followed in a second portion by a sharp rise of the force as far as a first maximum value (b) (first extreme point of the curves), which is necessary in order to allow the closing element to pass the first protrusion 10. This force then falls as far as a second extreme point (c), which defines the force (which is then only slightly rising due to the slightly conical design of the opening channel, see portion (d)) which is necessary to displace the ball in the closing portion 11. This force corresponds substantially to the force that is produced from the friction between the wall of the opening channel in the closing portion 11 and the contacting portion of the closing element 8. If a closing process is carried out correctly, the exertion of force ends anywhere in portion (d) of FIG. 7.

If the ram 13 dips too deeply into the opening channel however, the closing element may be pressed thereby against the second protrusion 12, which is again evidenced by a sharp rise in force (portion (e)). This rise may be limited (that is to say in accordance with the depth of dip of the ram 13) by the breaking load of the sample container 1 (and, where appropriate, also of the closing element 8 or of the ram 13) ((f)), whereby the force falls to a considerably lower level (portion (g)).

FIG. 7*b* shows a corresponding exemplary force curve for the use of a ram according to FIGS. 5 and 6. The force curve in portions (a) and (d) as well as therebetween corresponds to that in FIG. 7*a*. After portion (d), there is then a rise in force (h), which is sharper than that with the curve according to FIG. 7*a*. This is produced as a result of the contact between the ram 13 and the edge of the sample container 1. The ram 13 should then only be moved further over a relatively short path in order to avoid overloading the sample container 1 (or the ram 13). To control the stroke of the ram, the force curve can be evaluated such that, for example once the end of the portion (h) has been reached, a (force) limit value is reached, which for example may lead to a deactivation of a ram drive. In FIG. 7*b*, the further force curve that leads to a rupture of the sample container due to overload is also illustrated with a dashed line arrangement. This is characterized by a continuation of portion (h) (portion (i)), at the end of which the rupture occurs. This is characterized by a direct fall in force to a level close to zero (portion (k)).

Figure 20A:
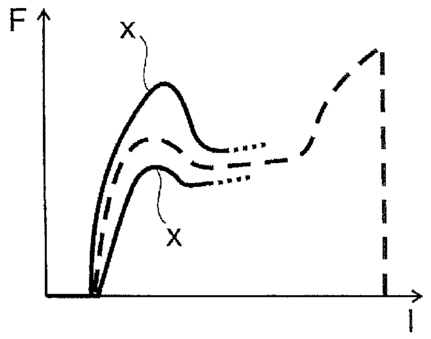
Figure 20B:
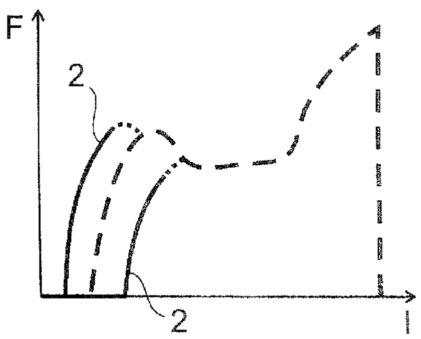
Figure 20C:
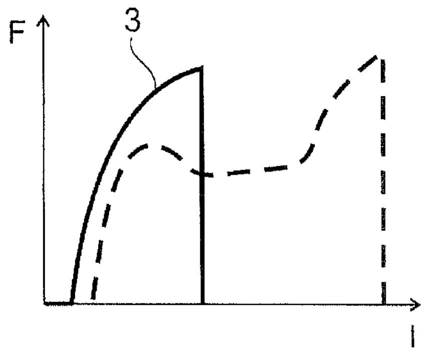
Figure 20D:
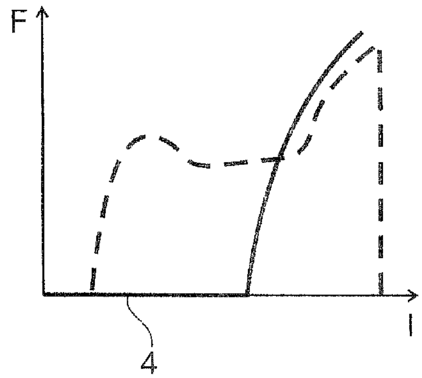
Figure 20E:
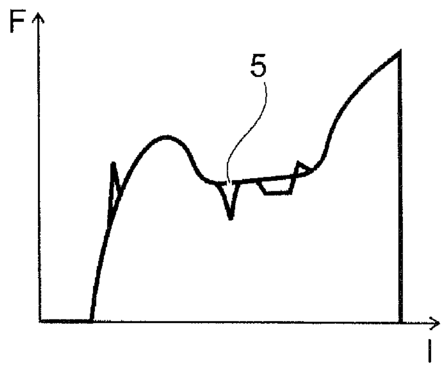
Figure 20F:
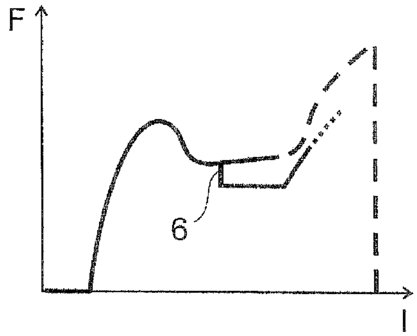

FIGS. 20*a* to 20*f* show exemplary deviations from the "normal" force curves described previously. It is possible to determine the appropriate fault source from these deviations. Here, the deviating force curve is illustrated by a continuous line, whereas the "normal" force curve is shown in a dashed manner. FIG. 20*a* shows two deviating force curves, wherein the dimensioning or the material properties of the sample container in the region of the opening channel and/or of the closing element are not correct. FIG. 20*b* shows two deviating force curves, wherein the vertical alignment of the closing element, that is to say the distance between the closing element and the ram, is too little or too large. In the case of the deviating force curve according to FIG. 20*c*, the horizontal alignment is not correct, that is to say there is insufficient conformity between the longitudinal axes of the sample container and of the ram. This may lead to an impairment of the movement of the closing element. FIG. 20*d* shows a deviating force curve which is produced if there is a fault concerning the closing element and the ram moves without substantial application of force until colliding with the sample container. The deviating force curve illustrated in FIG. 20*e* can be produced if the contact surfaces of the closing element and/or of the sample container do not correspond to the requirements. By contrast, FIG. 20*f* shows a deviating force curve which can be produced in the event of the rupture of a sample container.

FIGS. 8*a* and 8*b* show a second embodiment of a sample container 1, wherein two closing elements 8 are fixed in a force-locked manner in a common closing portion 11 of the housing 2. A second sample space is thus formed between the two closing elements 8. The corresponding embodiment of the opening channel, by contrast with the illustration in FIG. 8, can be selected arbitrarily in accordance with the exemplary embodiment according to FIGS. 1 to 3, that is to say in particular can be provided with one or more protrusions. Furthermore, a bypass channel 14 is formed in the wall of the housing between the lower sample space and the closing portion 11 and also between the closing portion 11 and the upper, open end of the sample container. The upper bypass channel 14 is used to balance an overpressure in the two sample spaces, which would otherwise be produced as a result of the relatively deep introduction of the closing elements. By contrast, the lower bypass channel 14 is provided, for example within the scope of the PCR process, to transfer a sample contained in the upper sample chamber into the lower sample chamber, as is illustrated in FIG. 8*a*. To this end, the lower closing element 8 is slid by means of the upper closing element 8 into the portion of the opening channel/sample space comprising the lower bypass channel 14, such that the sample can flow from the upper sample chamber via the lower bypass channel 14, past the lower closing element 8, and into the lower sample chamber.

FIGS. 9*a* to 9*b* show a sample container 1 in a further embodiment, in which said sample container is to be opened again by pressing the closing element 8 by means of a ram 13 completely into the sample space as far as the closed end. The sample liquid displaced during this process can flow off via a bypass channel 14 formed on one side in the wall of the housing 2 and can thus be removed from the sample container 1.

FIG. 10 shows a sample container 1, wherein the housing 2 is provided in the region of the sample space with a varying wall thickness. In the region of the sample space which receives the sample, the housing 2 has a minimal wall thickness, for example from 0.2 to 0.3 mm. A thin wall thickness simplifies the examination of the sample by means of optical methods. In a portion of the sample space which forms a dead space (that is to say with no sample contained therein), the wall thickness is thicker, by contrast (for example twice as thick, for example 0.4 to 0.6 mm), whereby not only can the mechanical stability of the housing 2 be increased, but in particular also an evaporation of the sample through the housing 2 can be reduced.

FIGS. 11 and 12 show individual components of an automated closing device (see FIG. 17) which is to be used in a device for carrying out a PCR process (see FIG. 18).

Here, FIG. 11 shows a storage container 15, in which a drawn-out guide 16 running in a spiraled manner is arranged and is used to receive and guide a multiplicity of closing elements 13 of a sample container 1. The lower end of the guide 16 ends in an outlet opening, via which the closing element can be transferred to a closing unit 17, as is illustrated in part in FIG. 12. The storage container 15, which can be sold as a filled disposable container, can be fastened for this purpose to the front end of the closing unit 17.

The closing unit 17 comprises an electric motor arranged in a housing 18, said electric motor being able to drive a drive disc 19 in rotation. The drive disc 19 is provided decentrally with a bolt 20, which is guided in a slot 21 of a ram guide 22. The guidance of the bolt 20 in the slot 21 translates the rotational movement of the drive disc 19 into a cyclical upward and downward movement of the ram guide 22, inclusive of a ram 13 fastened thereto, as is illustrated in principle in FIG. 13. With each downward movement of the ram 13, a closing element 8 held in a transfer position is entrained and is pressed via a discharge opening of the closing unit into the opening channel of a housing 2 of a sample container 1 arranged therebelow (not illustrated in FIG. 13). Once the ram 13 has been raised again, a further one of the closing elements 8 stored temporarily in succession in a feed channel 23 can then roll (as a result of the force of gravity) into the transfer position, where it is held via a spring-mounted barrier element 24. With the subsequent downward movement of the ram 13, the next closing element 8 is then entrained, wherein the barrier element 24 is displaced to the side in order to release the discharge opening.

Alternatively, it is also possible for the movement back and forth of the ram 13 to be caused not by a unidirectional rotation (through 360°) of the drive disc 19, but for said drive disc to also be drivable by means of a stepper motor having a (cyclical) rotational direction change in order to move the ram 13. Any, and in particular even changing, displacement paths, speed profiles, etc. of the ram 13 can thus be implemented. This can be used in particular to limit the force exerted by the ram 13 onto the closing element 8 (in conjunction with a measurement process using sensors) by means of a corresponding control of the stepper motor. This embodiment can also be developed such that the cyclical movement of the ram 13 is produced in principle by a continuous rotation of the drive disc 19, and the drive motor only stops the movement and reverses its direction of movement if there is a risk that the permissible force will be exceeded.

FIG. 14 shows a storage container 15*a* for a multiplicity of closing elements 8 in an alternative embodiment. The main differences from the storage container 15 according to FIG. 11 lie in the fact that on the one hand the closing elements 8 are stored in an unsorted manner, that is to say as a packing, in a storage space of the storage container 15*a* and on the other hand a ram 13*a* for dispensing the closing elements 8 individually from the storage container 15*a* is integrated. The base and wall surfaces of the storage container 15*a* are formed such that the closing elements arranged at the bottom in the packing are fed to a dispensing channel 29, of which the inner diameter is only slightly larger than the outer diameter of the closing elements. It is thus ensured that the closing elements reach a transfer position individually, where they can be caught and entrained by the ram 13*a*.

FIG. 15 shows the use of the storage container according to FIG. 14 in combination with an alternative closing unit 17*a* (only illustrated in part). A particular feature of this combination is for use of a total of two rams, on the one hand the ram 13*a* integrated into the storage container 15*a* for dispensing the closing elements 8 individually from the storage container, whereby the closing elements are placed on a sample container 1 arranged beneath. By contrast, a second ram 13 integrated into the closing unit 17*a* is used to drive the closing element 8 placed beforehand on a (different) sample container 1 into the closing portion of the opening channel of this sample container. The main advantage of the use of two rams lies in improved hygiene when the storage container 17*a*, inclusive of the ram 13*a*, is to be used as a disposable container, which is therefore disposed of after use.

As can be seen from FIG. 15, the movements of the two rams 13, 13*a* are coupled to one another. To this end, a bolt 30, which is spring-mounted in a portion of the ram 13, engages in a corresponding opening in the ram 13*a*. The movement of the ram 13 is thus transmitted to the ram 13*a*. The ram 13 itself is constructed in a number of parts and comprises a ram element 31, which is mounted in an axially displaceable manner in the lower end of a main body 32 of the ram 13. The ram element 31 is connected via a central bore with an inner thread to a threaded pin 33, which is part of a force limitation unit. The force limitation unit additionally comprises a spring 34 (cylindrical helical spring), which is biased by two contact plates 35. The bias forces are supported here via an abutment of the upper contact plate 35 and an annular protrusion of the ram element 31 against corresponding contact areas of the main body 32. The bias of the helical spring can be changed via the depth to which the threaded bolt 33 is screwed into the ram element 31, and a limit value for the force exerted by the ram element 31 onto the closing element 8 can thus be adjusted. As soon as this force is exceeded, the ram stroke is compensated for (partially) by a retreat of the ram element 13.

FIG. 16 shows a closing unit 17*b*, which corresponds substantially to that of FIG. 15 in terms of function, but is of simpler construction however. A (mechanical) force limitation unit is not provided here, rather this is achieved electronically by a corresponding controller of the ram drive. The ram element 31*a* is therefore integrated in the main body 32*a* of the ram 13 in an axially stationary manner, and the bolt 30*a* for entrainment of the ram 13*a* of the storage container also is not spring-mounted. In this case, the storage container 15*a* corresponds to that of FIG. 15.

The closing units 17, 17*a*, 17*b* and storage containers 15, 15*a* can be integrated into an automatic closing device 25, as is illustrated in FIG. 17. There, the unit formed from a closing unit 17 and storage container 15 can be displaced by a linear drive 26 along a first axis (in the transverse direction).

The automatic closing device according to FIG. 17 can in turn be integrated into a device for carrying out a PCR process according to FIG. 18, in such a way that the closing device 25 as a whole is displaceable by a second linear drive 27 along a second axis (in the longitudinal direction), which is oriented perpendicularly to the first axis (the axis of displacement of the linear drive 26 of the closing device). The displaceability of the unit formed of the closing unit 17 and storage container 15 in two axes oriented perpendicularly to one another makes it possible to remove a multiplicity of housings 2 of sample containers 1, which are positioned in a number of rows in a total of three sample container supports 7, and to close each of said housings with a closing element 8. The correct placement of the closing element 8 in the individual housings 2 is checked here with the aid of a laser distance sensor (not illustrated).

Figure 19:
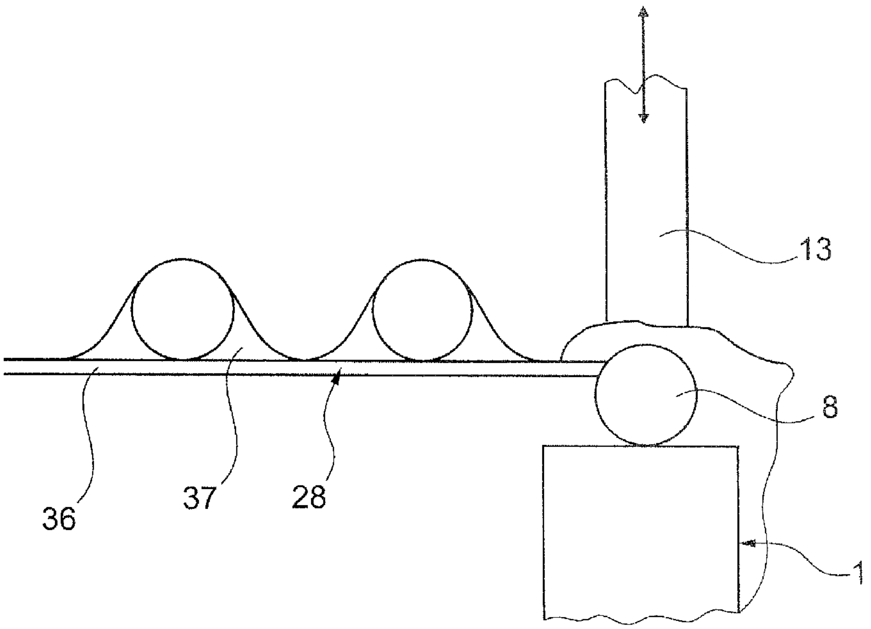

FIG. 19, in a schematic illustration, shows the possibility of fixing the closing elements 8 releasably in a conveyor belt (blister tape) 28 and of positioning said closing elements successively over a movement of the conveyor belt 28 in the transfer position, from which they can then be introduced by means of a ram 13 into the opening channel of a sample container 1. The conveyor belt 28 has a main belt 36 provided with openings arranged at regular intervals, wherein, in the region of each of the openings, a closing element 8 rests on one side of the main belt 26 and is surrounded there by a retaining belt 37 and is thus held in place. The individual closing elements can be removed from the conveyor belt 28 through the prospective opening and driven into the opening channel of the sample container 1 by means of the ram 13.

The invention claimed is:

1. A sample container, comprising:

a housing which forms a sample space for receiving a sample and has at least one circular opening at one end which extends in an opening channel into the sample space, and a spherical closing element, wherein the diameter of the closing element only exceeds the diameter of the opening channel in at least one closing portion to such an extent that the closing element can be fixed in a force-locked manner by a largest circumference thereof in the at least one closing portion, wherein the closing element is spherical and in contact with the housing, and further wherein the opening channel from the at least one closing portion to an inner opening forms a protrusion, which reduces an opening cross section of the opening channel with respect to the opening cross section in the at least one closing portion, and further wherein the opening channel from the at least one closing portion to the at least one circular opening forms a further protrusion, which reduces the opening cross section of the opening channel with respect to the opening cross section in the at least one closing portion, wherein the distance from the further protrusion to the protrusion permits a positioning tolerance of the closing element of from 0.7 mm to 5 mm, and wherein the housing is formed in a tapering manner at a second end.

2. The sample container as claimed in claim 1, wherein the opening cross section of the opening channel in a region of the further protrusion is larger than that in the region of the protrusion.

3. The sample container as claimed in claim 1, wherein the opening channel is cylindrical in a region of the at least one closing portion.

4. The sample container as claimed in claim 1, wherein the housing is tubular.

5. The sample container as claimed in claim 1, wherein the housing is optically transparent at least in a portion of the at least one closing portion and/or in a tapering end thereof.

6. The sample container as claimed in claim 5, wherein the wall thickness of the housing varies from 0.2 to 0.3 mm in a region of the tapering end to 0.4 to 0.6 mm in at least one second region of the sample space.

7. The sample container as claimed in claim 1, wherein the housing forms a shoulder.

8. The sample container as claimed in claim 1, wherein the housing, at least in the at least one closing portion of the opening channel, and the closing element are formed from materials having identical coefficients of thermal expansion.

9. The sample container as claimed in claim 1, wherein the closing element is formed from an electrically conductive material.

10. The sample container as claimed in claim 1, wherein the closing element is formed from a material that is not fluorescent.

11. The sample container according to claim 1, wherein the housing is provided with a breaking point at which the housing may be separated by a defined application of force.

12. The sample container as claimed in claim 1, comprising a second closing portion for a second closing element, wherein a second sample space is formed between the two closing elements.

13. The sample container as claimed in claim 12, wherein a bypass channel is provided in a wall of the housing between the two closing portions.

* * * * *